(12) United States Patent
Schmotzer

(10) Patent No.: US 7,364,685 B2
(45) Date of Patent: Apr. 29, 2008

(54) METHOD FOR PRODUCING IMPLANT PARTS FROM HIGHLY CROSS-LINKED UHMWPE AND IMPLANT PARTS FOR HUMAN MEDICINE

(75) Inventor: Hans Schmotzer, Zurich-Alstetten (CH)

(73) Assignee: Plus Orthopedics AG, Rotkreuz (CH)

( * ) Notice: Subject to any disclaimer, the term of this patent is extended or adjusted under 35 U.S.C. 154(b) by 216 days.

(21) Appl. No.: 10/468,673

(22) PCT Filed: Jan. 31, 2002

(86) PCT No.: PCT/EP02/01011

§ 371 (c)(1),
(2), (4) Date: Feb. 20, 2004

(87) PCT Pub. No.: WO02/062548

PCT Pub. Date: Aug. 15, 2002

(65) Prior Publication Data

US 2004/0132852 A1    Jul. 8, 2004

(30) Foreign Application Priority Data

Feb. 5, 2001    (DE)    ................. 101 05 085

(51) Int. Cl.
| | |
|---|---|
| B29B 13/08 | (2006.01) |
| C08J 3/28 | (2006.01) |
| C08F 110/02 | (2006.01) |
| A61F 2/02 | (2006.01) |
| A61F 2/28 | (2006.01) |
| A62L 27/16 | (2006.01) |

(52) U.S. Cl. .................. 264/489; 264/494; 522/161; 526/352; 623/23.58

(58) Field of Classification Search ............... 522/161; 264/442, 489, 494, 289; 526/352; 623/23.58
See application file for complete search history.

(56) References Cited

U.S. PATENT DOCUMENTS

| | | | |
|---|---|---|---|
| 5,414,049 A | 5/1995 | Sun et al. | |
| 5,577,368 A | 11/1996 | Hamilton et al. | |
| 5,753,182 A * | 5/1998 | Higgins | ................. 422/23 |
| 5,814,266 A * | 9/1998 | Pienkowski et al. | ......... 264/443 |
| 6,017,975 A | 1/2000 | Saum et al. | |
| 6,165,220 A | 12/2000 | McKellop et al. | |
| 6,174,934 B1 | 1/2001 | Sun et al. | |
| 6,228,900 B1 | 5/2001 | Shen et al. | |
| 6,395,799 B1 * | 5/2002 | Johnson | ................. 522/161 |
| 2003/0234459 A1 * | 12/2003 | Nandu et al. | ............. 264/1.36 |

FOREIGN PATENT DOCUMENTS

| | | |
|---|---|---|
| EP | 0 737 481 A1 | 4/1996 |
| EP | 0 722 973 | 7/1996 |
| EP | 1 072 274 A1 | 7/2000 |
| EP | 1 072 275 A1 | 1/2001 |
| EP | 1 086 709 A1 | 3/2001 |
| WO | WO 97/29793 | 8/1997 |
| WO | WO98/01085 | 1/1998 |
| WO | WO98/14223 | 4/1998 |

OTHER PUBLICATIONS

Japanese Office Action, mailed Dec. 1, 2006, for related Japanese Patent Application (JP 2002-562537).

* cited by examiner

Primary Examiner—Susan W. Berman
(74) Attorney, Agent, or Firm—Knobbe Martens Olson & Bear LLP

(57) ABSTRACT

The invention relates to a method of manufacturing implant parts made of highly cross-linked polyethylene, wherein a blank made of ultra-high-molecular-weight polyethylene is irradiated with ionizing radiation in order to produce radicals in the blank. To optimize the cross-linkage of the highly cross-linked polyethylene and to eliminate free radicals, the blank is subsequently treated by means of microwave radiation and/or ultrasound in such a way that free radicals, which have not recombined, are excited so as to ensure substantially complete recombination of the free radicals. The shape of the treated blank can then be adjusted by means of machining. The invention further relates to implant parts for application in human medicine that have been manufactured as described above.

27 Claims, No Drawings

METHOD FOR PRODUCING IMPLANT PARTS FROM HIGHLY CROSS-LINKED UHMWPE AND IMPLANT PARTS FOR HUMAN MEDICINE

REFERENCE TO RELATED APPLICATIONS

This is a U.S. national phase application of PCT application number PCT/EP02/01011, filed Jan. 31, 2002 claiming priority to German patent Application number 101 05 085.2, filed Feb. 5, 2001.

BACKGROUND

1. Field of the Invention

The present invention relates to a method of manufacturing implant parts made of highly cross-linked polyethylene, in the following termed UHMWPE (ultra-high molecular weight polyethylene), as well as to parts of an implant for application in human medicine. Often such parts are used as a covering layer and/or as a material for slide bearings, provided in order to optimize physicomechanical properties.

2. Description of the Related Art

In the past "normal" UHMWPE was used for this purpose, but it proved to have undesired physiologically relevant side effects ascribable to inadequacy of that form of UHMWPE with respect to homogeneity and resistance to abrasion. For example, when "normal" UHMWPE is used as a sliding bearing in artificial hip joints, abrasion produces microscopically small particles that become distributed in the surrounding tissue and can produce tissue necrosis and osteolysis. The body reacts with inflammations and tissue alterations. Hence a long-term employment of such implant parts—although highly desirable in itself—is impossible. Repeated operations are needed.

Subsequently, therefore, the material used for such implant parts was highly cross-linked polyethylene that had been produced from conventional UHMWPE by additional cross-linking steps. This cross-linkage was customarily achieved by way of intermediate stages involving radicals that are produced either by means of ionizing radiation or, as an alternative, by chemical means.

An essential prerequisite for the application within an organism of the highly cross-linked polyethylene thus produced, however, is that the radicals appear merely in a transitional state and are completely eliminated by subsequent reactions; otherwise, as is generally known, the radicals could bring about destruction of tissue, for instance by acting as carcinogens.

Complete elimination of the radicals, however, has proved problematic, because their stability and hence their lifespan is "positively" influenced by various kinetic and/or thermodynamic effects. In the matrix of interest here, namely cross-linked polyethylene, the alkyl groups have a stabilizing action and there is also a steric intervention by substituents with a blocking action owing to strong cross-linkage, or reduced mobility resulting from the strong cross-linkage, so that some radicals hardly have any opportunity for recombination and thus remain more or less isolated in the matrix—although in principle, later reactions can allow diffusion of these radicals.

The ultimate result is that incomplete elimination of the radicals impairs the properties of the implant part, for instance by subsequent oxidation, and hence leads to the problems cited above with respect to the homogeneity and resistance to abrasion of the polyethylene of which that part is made.

This problem has long been acknowledged, and attempts have been made to solve it in various ways.

These approaches are based substantially on tempering the workpiece at an elevated temperature, in the region of its melting point, in order to increase the mobility of the radicals remaining in the workpiece and enable their recombination.

Such a procedure is described, for example, in the patent U.S. Pat. No. 6,017,975, which proposes heating of the irradiated matrix to a temperature of about 150° C. until substantially all the free radicals are recombined. What is not considered here, however, is that whereas heating the matrix does make it semifluid on account of its high degree of cross-linkage, heating alone cannot eliminate the steric interference caused by the cross-linkage, so that although the mobility of the radicals is somewhat increased, a reaction of all the radicals, especially the sterically hampered ones, is practically impossible within a reasonable period of time.

In the end result this means that the time required for recombination of all free radicals, in particular also because the structure of the matrix is not constant from one case to another, is unpredictable and can be almost arbitrarily long.

A similar approach has been taken in the patents U.S. Pat. No. 5,414,049 and EP 0 722 973 A1. There the irradiated matrix is likewise tempered; in the US document the objective is likewise to eliminate free radicals, whereas in the EP document this is merely a concomitant reaction, the main goal being that the tempering should prevent the possibility of later shrinkage of the matrix. The problems associated with tempering alone, as described above, also apply to these last two patent documents.

A completely different approach is that of U.S. Pat. No. 5,577,368, the objective of which is to use an external hydrogen partial pressure during irradiation in order to reduce the number of remaining free radicals. Here the disadvantage is that the cross-linkage of the polythene is diminished in comparison to the methods cited above, because breaks in the chain binding can be filled in by saturation with hydrogen, without the formation of a carbon-carbon bond.

The patent WO 97/29793 A1 describes prostheses made of irradiated UHMWPE and other objects consisting of this material, in each case without free radicals, as well as several methods of manufacturing such UHMWPE, in which the irradiation is carried out exclusively with electron beams.

The patent EP 1 072 274 A1 describes a method of manufacturing sliding-bearing layers, in which a polymeric material, preferably UHMWPE, is exposed to irradiation with gamma rays in order to bring about a desired degree of cross-linkage. This material is then cross-linked at a temperature above the melting point to increase its ability to resist oxidative decomposition. Subsequently the product is shaped as desired and again irradiated with gamma rays to sterilize it.

The patent EP 1 072 275 discloses a method of manufacturing sliding-bearing layers made of UHMWPE for orthopedic implants, in which a cross-linkage of the polymers is brought about by irradiation with gamma rays, X-rays, ultraviolet rays, or neutron, proton or electron beams, in order to cross-link at least part of the UHMWPE.

Finally, the patent EP 1 086 709 A1 discloses a method of improving the sliding-bearing properties of molded parts made of UHMWPE for orthopedic implants, in which the UHMWPE is irradiated with electron beams and thus a reduction or elimination of the free radicals and cross-linkage of the product are achieved.

SUMMARY

In none of the methods cited above is a subsequent treatment performed in such a way that free radicals that have not been substantially recombined are excited by means of microwave radiation and/or ultrasound.

Accordingly, the objective of the present invention is to make available a method of manufacturing implant parts in which the UHMWPE is, firstly, highly cross-linked, and in which furthermore the radical content is reduced in comparison to the state of the art. A further objective of the invention resides in achieving these goals by means of subsequent treatment in a manner that is as gentle as possible, in that it avoids high processing temperatures. The invention thus makes it possible to achieve a cross-linkage density similar to that in the previously known products as well as a reduction of the free radicals, at distinctly lower processing temperatures.

DETAILED DESCRIPTION OF THE PREFERRED EMBODIMENTS

This objective is achieved by a method of manufacturing implant parts made of highly cross-linked polyethylene that comprises the following steps:
  irradiation of a blank made of ultra-high-molecular-weight polyethylene with ionizing radiation, in particular by X-rays, gamma rays or electron beams, in order to produce radicals,
  subsequent treatment of the irradiated blank,
  adapting the shape of the treated blank so as to produce an implant part,
  wherein the subsequent treatment consists in exciting free radicals, which have not recombined, by means of microwave radiation and/or ultrasound so as to ensure substantially complete recombination of the free radicals. As a result, the cross-linkage of the UHMWPE is also further optimized. Another objective of the invention is the employment of the products thus manufactured as implant parts for application in human medicine.

The essential idea of the invention resides in the fact that molecules and/or parts of molecules with a polar structure can be excited by means of microwave radiation. This excitation is brought about in the immediate surroundings of the polar structural element, for instance the macromolecule, and leads indirectly to a heating of the polar components. No heating of the further surroundings of the polar structural element is caused by the microwave radiation; such warming as may occur would be ascribable to heat conduction within the matrix. Hence the microwave radiation makes it possible to restrict heating within the matrix to the immediate vicinity of the radicals.

The increased kinetic energy of the free radicals and their surroundings in turn results in an increased mobility of the electrons involved, and hence to a migration of the radical's electron, for example by isomerization, until a suitable reaction partner such as another radical's electron comes within range and the two electrons recombine, forming a new σ bond.

When microwave radiation is used to promote the recombination of free radicals it is in principle possible to begin irradiating the matrix that contains the radicals at room temperature, which will cause its temperature to rise. However, it is also possible to reinforce this process by additionally heating the matrix in the conventional manner. For example, by this means a residual heat resulting from a completed treatment with ionizing radiation can be exploited, insofar as the blank has been heated prior to the irradiation. Renewed heating is of course also possible.

The essential effect of the invention, namely the additional temperature elevation in the immediate vicinity of polar structures in the matrix as compared with the surroundings, is substantially uninfluenced by conventional heating; all that results is an increase in the speed of diffusion or migration velocity of the radical's electrons brought about by the rise in temperature.

In the absence of conventional prior heating of the matrix, the temperature of the blank, i.e. of the matrix that forms the blank, can also be warmed sufficiently to achieve an acceptable reaction speed by microwave radiation alone. This is the case, for example, when the energy density of the microwave radiation applied to the blank is in the range from $10$ mW/cm$^2$ to $10$ W/cm$^2$ and preferably in the range from $100$ mW/cm$^2$ to $5$ W/cm$^2$. By this means it is possible to reach a temperature in the blank of more than $60°$ C., e.g. up to but not including its melting point, preferably in the range from $80°$ C. to $140°$ C., and particularly preferably up to $130°$ C.

The frequencies of the microwave radiation applied to the blank are in general in the range between $20$ MHz and $300$ GHz, the frequencies in any particular case being adjusted in particular so as to induce carbon-carbon and carbon-hydrogen binding in the vicinity of the radicals.

In accordance with the invention it is possible to carry out the subsequent treatment of the irradiated blank exclusively with microwave radiation. Furthermore, ultrasound can be used to supplement or replace microwave radiation. The latter option exploits the effect that ultrasound causes very high-frequency mechanical vibration that warms the interior of the exposed object. In this case the blank can exposed, and hence heated, as a whole; however, because ultrasonic waves can be so readily focused, it is also possible to apply them in bundled form so that they act on certain selected regions of the blank, for instance by sweeping along a raster.

When ultrasound is used as energy carrier, preferably a sound intensity in the range from $0.2$ W/cm$^2$ to $20$ W/cm$^2$ is employed; this is sufficient to heat the blank up to or even above its melting point. As a result, the diffusion velocity of the free radicals in turn increased. Preferably the sound intensity is in the range from $1$ W/cm$^2$ to $15$ W/cm$^2$, and especially preferably in the range from $5$ W/cm$^2$ to $10$ W/cm$^2$. In addition, in the fluid phase of the matrix sonochemical reactions are possible, based on cavitation. Such cavitation is associated with extremely high temperatures lasting for only a short time, which cause molecular dissociation and a subsequent recombination of the radicals thus produced, which enhances the migration ability of the original radical electron.

The employment of a conventional means of heating, not based on exposure to ultrasound, is also possible as a supplementary measure. Here, again, the residual heat from the preceding irradiation step can be utilized.

In a combination of microwave radiation with exposure to ultrasound, the positive actions of the two energy carriers as described above are reciprocally supplementary.

Irradiation of the blank and the subsequent treatment in accordance with the invention are performed with a radiation device disposed substantially parallel to the smallest dimension of the blank, i.e. the thickness; here the thickness of the blank is in the range from $0.5$ cm to $10$ cm, preferably in the range from $1$ cm to $7$ cm, and particularly preferably not more than $4$ cm. By choosing this direction of the rays a maximal penetration is achieved.

As ionizing radiation electron radiation is used, alternatively or as a supplement thereto gamma radiation and/or X-radiation. Of these, electron radiation is preferred, because the time required to induce radical formation is shorter and hence the possibility of oxidation—insofar as oxygen is not excluded during the irradiation—is diminished. Furthermore, by varying the energy of the electrons the penetration depth of the electrons can be varied, thus affecting the degree of cross-linking and the crystallinity of the UHMWPE product. The applied energy here is generally in the range from 0.5 MeV to 15 MeV, preferably in the range from 5 MeV to 12 MeV, and particularly preferably in the range from 8 MeV to 11 MeV, e.g. about 10 MeV.

Gamma radiation is preferred when great penetration depths are required. The applied dose in this case is generally in the range from 2.5 Mrad to 25 Mrad, preferably in the range from 4 Mrad to 16 Mrad, and particularly preferably from 8 Mrad to 12 Mrad, e.g. about 10 Mrad.

Irradiation of the blank with ionizing rays is also generally carried out at a temperature up to but not including its melting point, in particular in the range from 60° C. to 160° C., preferably in the range from 80° C. to 140° C., and particularly preferably in the range from 110° C. to 130° C. In comparison to irradiation at room temperature, which is likewise possible, the elevated temperature is advantageous inasmuch as the amorphous portion of the blank matrix is increased. The consequence is that the crystallinity and thus also the danger of fracture formation in the blank are reduced. Furthermore, the mobility of the individual molecule chains is increased and enables good cross-linkage under irradiation. In addition, the reaction speed of cross-linking rises with the temperature.

According to another embodiment of the invention, during and/or after irradiation with the ionizing rays the blank goes through a tempering phase with a duration of up to one day, preferably up to about 12 hours, and particularly preferably for a period of 2 hours to 4 hours, during which the temperature is in the temperature ranges given above.

The advantage of such tempering is that free radicals, which have not yet been eliminated by reaction or recombined by a σ-bond and are unhindered either thermodynamically or kinetically, can to a great extent undergo such reactions during the tempering phase.

According to an especially advantageous embodiment of the method, the irradiated blank is subsequently treated during the tempering phase with microwave radiation and/or ultrasound, and to reinforce their actions an elevated temperature is employed, in particular the temperature that is maintained throughout the tempering phase.

After the treatment with microwaves and/or ultrasound and the tempering phase the blank is cooled to room temperature according to a pre-specified cooling program, during which process care should be taken to keep the blank free of tension. This is possible in accordance with the invention in that the cooling is done at a rate in the range of 1° C. to 10° C. per hour, preferably at 2.5° C. to 7° C. per hour and particularly preferably at substantially 5° C. per hour.

By this means, especially in combination with the preceding tempering phase, it is possible to avoid later shrinkage of the blank.

According to a further embodiment of the method in accordance with the invention, at least partial steps of the method are carried out under subatmospheric pressure, for example in a vacuum, e.g. that of a glass filter pump or in high vacuum. This has the advantage that reactions of the blank matrix with the surrounding gas are minimized or avoided. An especially advantageous result is the prevention or minimization of oxidation, which would otherwise cause brittleness and ageing of the finished product.

Furthermore, it is possible to carry out at least partial steps of the method under an oxygen- and/or moisture-reduced atmosphere and/or under inert gas.

Partial steps of the method in both cases should be understood to mean in particular the irradiation, tempering, cooling and subsequent treatment phases.

Instead of a pressure below atmospheric pressure, another possible means of avoiding oxidation is to exclude or at least reduce the content of oxygen and/or moisture in the atmosphere that surrounds the blank. Complete replacement of atmospheric air with a gas that is slow to react or inert is also possible. Gases suitable for this purpose, for example, are nitrogen or the noble gases, in particular argon.

According to another advantageous embodiment of the invention, the subsequent treatment in accordance with the invention is carried out in an atmosphere enriched with hydrogen. The advantage resulting in this case resides in the high diffusion capacity of hydrogen. The hydrogen can diffuse into the polymer matrix and react with free-radical electrons to form a carbon-hydrogen bond. Furthermore, hydrogen is suitable for producing a reducing atmosphere that counteracts the possibility of oxidation.

It is advantageous for the shape of the blank to be adjusted, after all treatments are completed, by machining.

In its second aspect, the objective of the present invention is achieved by employing a highly cross-linked polyethylene that has been treated according to the present method as part of an implant.

The advantage here is that such a highly cross-linked polyethylene is particularly resistant to abrasion and contains practically no free radicals. An implant part thus produced therefore presents no physiological risks, as opposed to conventionally known implant parts, and has greatly increased biocompatibility and hence useful life in comparison to known implant parts.

In the following the invention is explained with reference to an exemplary embodiment.

EXAMPLE

A 40-mm-thick piece of UHMWPE intermediate product, commercially available for example as GUR 1020 (specific weight: 927-944 g/l, molecular weight: 3-4 million g/mol, no stabilizer) according to ISO 5834-2 is used as a blank. After heating for 3 hours in an oven that has been preheated to 125° C. this blank, now itself at 125° C., is irradiated with electrons having an energy of 10 MeV in a beam directed parallel to the smallest dimension of the blank. The total power is 120 kW. Subsequently the blank, still at the same temperature, is exposed to microwaves having an energy of 2 W/cm$^2$ and ultrasound, likewise at 2 W/cm$^2$, for 30 minutes and then cooled to room temperature at a constant rate of 5° C. per hour. Further processing of the blank consists in machining it into a shape suitable for serving as sliding bearing for a hip prosthesis, against which the head of a hip-prosthesis shaft articulates.

What is claimed is:

1. A method of manufacturing implant parts made of highly cross-linked polyethylene comprising substantially no free radicals, said method comprising:
   irradiating a blank made of ultra-high-molecular-weight polyethylene with ionizing radiation, said ionizing radiation selected from the group consisting of X-rays, gamma rays and electron beams, in order to produce free radicals in the blank,
   subsequently substantially recombining the free radicals in the blank that have not recombined by applying microwave radiation to the blank at a temperature up to but not including its melting point, said application of microwave radiation ensuring substantially complete recombination of the free radicals;

shaping the blank so as to produce an implant part.

2. The method according to claim 1, wherein microwave radiation is applied to the blank at frequencies in the range between 20 MHz and 300 GHz, the applied frequencies being adjusted so as to induce carbon-carbon and carbon-hydrogen bonding in the vicinity of the radicals.

3. The method according to claim 1, wherein the irradiating comprises directing radiation substantially parallel to a thickness dimension of the blank, the thickness of the blank being in the range from 0.5 cm to 10 cm.

4. The method according to claim 3, wherein the irradiating comprises directing radiation substantially parallel to a thickness dimension of the blank, the thickness of the blank being in the range from about 1 cm to 7 cm.

5. The method according to claim 4, wherein the irradiating comprises directing radiation substantially parallel to a thickness dimension of the blank, the thickness of the blank being less than 4 cm.

6. The method according to claim 1, further comprising:
heating the blank to a temperature in the range from 60° C. to 160° C. before or during irradiation with the ionizing radiation;
maintaining the blank at the temperature to which it has been heated during at least a portion of said irradiating and subsequently substantially recombining;
tempering the blank said tempering occurring at a temperature in the range of about 60° C. to about 160° C. for a duration of up to about one day; and
cooling the blank to room temperature with a cooling rate in the range from 1° C. to 10° C. per hour.

7. The method according to claim 6, wherein the subsequent substantially recombining the free radicals in the irradiated blank is carried out during the tempering phase or during cooling of the blank.

8. The method according to claim 6, wherein at least a portion of at least one of the irradiation, tempering, cooling and subsequent substantially recombining phase is carried out under subatmospheric pressure.

9. The method according to claim 8, wherein at least a portion of at least one of the irradiation, tempering, cooling and subsequent substantially recombining steps is carried out in a vacuum.

10. The method according to claim 6, wherein at least a portion of at least one of the irradiation, tempering, cooling and subsequent substantially recombining phases is carried out in a controlled atmosphere, wherein the atmosphere is controlled by performing at least one step selected from the group consisting of reducing an oxygen or moisture-content of the atmosphere, supplying an inert gas, and enriching a hydrogen-content of the atmosphere.

11. The method according to claim 9, wherein the subsequent substantially recombining phase is carried out in a hydrogen-enriched atmosphere.

12. The method according to claim 6, comprising:
heating the blank to a temperature in the range from about 80° C. to 140° C. before or during irradiation with the ionizing radiation;
maintaining the blank at the temperature to which it has been heated during said irradiating and subsequently substantially recombining;
tempering the blank after said irradiating and subsequently substantially recombining, said tempering occurring at the temperature to which it has been heated for a duration of up to 12 hours;
cooling said blank to room temperature at a cooling rate in the range from about 2.5° C. to about 7° C. per hour.

13. The method according to claim 12, comprising:
heating the blank to a temperature in the range from about 110° C. to about 130° C. before or during irradiation with the ionizing radiation;
maintaining the blank at the temperature to which it has been heated during said irradiating and subsequently substantially recombining;
tempering the blank after said irradiating and subsequently substantially recombining, said tempering occurring at the temperature to which it has been heated for a duration of about 2 to about 4 hours;
cooling said blank to room temperature at a cooling rate in the range from about 2.5° C. to about 7° C. per hour.

14. The method according to claim 1, wherein the shaping is by machining.

15. The method according to claim 1, wherein said irradiating comprises using an electron beam having an energy range from 0.5 MeV to 15 MeV.

16. The method according to claim 15, wherein said irradiating comprises using an electron beam having an energy range from 5 MeV to 12 MeV.

17. The method according to claim 16, wherein said irradiating comprises using an electron beam having an energy range from 8 MeV to 11 MeV.

18. The method according to claim 1, wherein said irradiating comprises using gamma radiation in a range from 2.5 Mrad to 25 Mrad.

19. The method according to claim 18, wherein said irradiating comprises using gamma radiation in a range from 4 Mrad to 16 Mrad.

20. The method according to claim 19, wherein said irradiating comprises using gamma radiation in a range from 8 Mrad to 12 Mrad.

21. The method according to claim 1, wherein ultrasound is additionally applied to the sample during the substantially recombining the free radicals in the irradiated blank.

22. The method according to claim 21, wherein the energy density of the microwave radiation applied to the blank is in the range from 10 mW/cm$^2$ to 10 W/cm$^2$, such that for its subsequent substantially recombining the free radicals in the blank, the blank is heated by microwave radiation and/or ultrasound to a temperature above 60° C.

23. The method according to claim 22, wherein the energy density of the microwave radiation applied to the blank is in the range from about 100 mW/cm$^2$ to about 5 W/cm$^2$, such that for its subsequent substantially recombining the free radicals in the blank, the blank is heated by microwave radiation and/or ultrasound to a temperature between 80° C. to 140° C.

24. The method according to claim 23, wherein the energy density of the microwave radiation applied to the blank is in the range from about 100 mW/cm$^2$ to about 5 W/cm$^2$, such that for its subsequent substantially recombining the free radicals in the blank, the blank is heated by microwave radiation and/or ultrasound to a temperature between 80° C. and 130° C.

25. The method according to claim 21, wherein ultrasound is applied with a sound intensity in the range from 0.2 W/cm$^2$ to 20 W/cm$^2$.

26. The method according to claim 25, wherein the sound intensity of the ultrasound is in the range from about 1 W/cm$^2$ to about 15 W/cm$^2$.

27. The method according to claim 26, wherein the sound intensity of the ultrasound is in the range from about 5 W/cm$^2$ to about 10 W/cm$^2$.

* * * * *

UNITED STATES PATENT AND TRADEMARK OFFICE
CERTIFICATE OF CORRECTION

PATENT NO. : 7,364,685 B2
APPLICATION NO. : 10/468673
DATED : April 29, 2008
INVENTOR(S) : Hans Schmotzer Page 1 of 1

It is certified that error appears in the above-identified patent and that said Letters Patent is hereby corrected as shown below:

In Specification (08/01/2003), Page 1, Title item (54); should read;
METHOD OF MANUFACTURING IMPLANT PARTS MADE OF HIGHLY CROSS-LINKED UHMWPE, AND PARTS FOR IMPLANTS APPLIED IN HUMAN MEDICINE, please incorporate the same Title in the Issued Patent, therefor.

Signed and Sealed this

Seventh Day of October, 2008

JON W. DUDAS
*Director of the United States Patent and Trademark Office*

UNITED STATES PATENT AND TRADEMARK OFFICE
CERTIFICATE OF CORRECTION

PATENT NO. : 7,364,685 B2  
APPLICATION NO. : 10/468673  
DATED : April 29, 2008  
INVENTOR(S) : Hans Schmotzer It is certified that error appears in the above-identified patent and that said Letters Patent is hereby corrected as shown below:

In Specification (08/01/2003), Page 1, Title item (54) and Column 1, lines 1-4; should read; METHOD OF MANUFACTURING IMPLANT PARTS MADE OF HIGHLY CROSS-LINKED UHMWPE, AND PARTS FOR IMPLANTS APPLIED IN HUMAN MEDICINE, please incorporate the same Title in the Issued Patent, therefor.

This certificate supersedes the Certificate of Correction issued October 7, 2008.

Signed and Sealed this

Twenty-first Day of October, 2008

JON W. DUDAS  
*Director of the United States Patent and Trademark Office*